United States Patent
LaPrade et al.

[11] Patent Number: 6,159,497
[45] Date of Patent: Dec. 12, 2000

[54] PATCH APPLICATOR

[75] Inventors: Ronald LaPrade; John J. Wick, both of Miami, Fla.

[73] Assignee: Noven Pharmaceuticals, Inc., Miami, Fla.

[21] Appl. No.: 09/368,014

[22] Filed: Aug. 3, 1999

Related U.S. Application Data

[63] Continuation-in-part of application No. 09/182,654, Oct. 30, 1998.

[51] Int. Cl.<sup>7</sup> .................................................... A61F 13/02
[52] U.S. Cl. ........................ 424/448; 424/449; 424/447; 600/47; 600/48; 600/59; 600/60
[58] Field of Search ................................. 128/155, 156; 424/448, 449

[56] References Cited

U.S. PATENT DOCUMENTS

| | | |
|---|---|---|
| Re. 33,353 | 9/1990 | Heinecke . |
| 2,579,403 | 12/1951 | Slomowitz et al. . |
| 2,629,378 | 2/1953 | Barton . |
| 2,969,057 | 1/1961 | Simmons . |
| 3,018,881 | 1/1962 | Wall et al. . |
| 3,120,229 | 2/1964 | Hinkamp . |
| 3,888,247 | 6/1975 | Stenvall . |
| 4,022,203 | 5/1977 | Ackley . |
| 4,176,664 | 12/1979 | Kalish . |
| 4,235,337 | 11/1980 | Dotta . |
| 4,513,739 | 4/1985 | Johns ...................................... 128/156 |
| 4,564,010 | 1/1986 | Coughlan et al. . |
| 4,598,004 | 7/1986 | Heinecke . |
| 4,600,001 | 7/1986 | Gilman . |
| 4,614,183 | 9/1986 | McCracken et al. .................... 128/186 |
| 4,638,043 | 1/1987 | Szycher et al. . |
| 4,767,401 | 8/1988 | Seiderman . |
| 4,815,457 | 3/1989 | Mazars et al. ........................... 128/155 |
| 4,832,008 | 5/1989 | Gilman . |
| 4,832,009 | 5/1989 | Dillon . |
| 4,911,707 | 3/1990 | Heiber et al. . |
| 4,915,950 | 4/1990 | Miranda et al. . |
| 4,917,676 | 4/1990 | Heiber et al. . |
| 4,919,648 | 4/1990 | Sibalis . |
| 4,926,850 | 5/1990 | Lott et al. . |
| 4,928,680 | 5/1990 | Sandbank . |
| 4,994,267 | 2/1991 | Sablotsky . |
| 5,018,516 | 5/1991 | Gilman . |
| 5,052,381 | 10/1991 | Gilbert et al. ........................... 128/155 |
| 5,074,293 | 12/1991 | Lott et al. . |
| 5,099,832 | 3/1992 | Ward . |
| 5,160,315 | 11/1992 | Heinecke et al. . |
| 5,266,371 | 11/1993 | Sugii et al. . |
| 5,275,284 | 1/1994 | Onotsky . |
| 5,300,291 | 4/1994 | Sablotsky et al. . |
| 5,336,162 | 8/1994 | Ota et al. . |
| 5,397,297 | 3/1995 | Hunter . |
| 5,415,626 | 5/1995 | Goodman et al. . |
| 5,415,627 | 5/1995 | Rasmussen et al. . |
| 5,417,674 | 5/1995 | Smith et al. . |
| 5,423,737 | 6/1995 | Cartmell et al. . |
| 5,437,622 | 8/1995 | Carion . |
| 5,462,746 | 10/1995 | Wolter et al. . |
| 5,476,443 | 12/1995 | Cartmell et al. . |
| 5,489,262 | 2/1996 | Cartmell et al. . |
| 5,520,629 | 5/1996 | Heinecke et al. . |
| 5,562,642 | 10/1996 | Smith et al. . |

*Primary Examiner*—Thurman K. Page
*Assistant Examiner*—Isis Ghali
*Attorney, Agent, or Firm*—Oldham & Oldham Co., L.P.A.

[57] ABSTRACT

A patch applicator for easy application of a transdermal patch is disclosed, wherein the applicator is especially suitable for a small transdermal patch of size 20 cm² or less. The patch applicator includes a rigid release liner and a flexible transdermal patch releasably attached to the release liner. The release liner has a first and second poritons separated by a slit, and pulltabs affixed to the portions. The pulltabs can extend beyond an end margin of the transdermal patch, and preferably extend outwardly at an acute angle for use, so that a patch user may easily grasp the pulltabs and remove a first portion of the release liner from the patch. The patch is then applied to the skin or mucosa, followed by removal of the second portion and final application of the patch. The patch applicator reduces loss in manufacturing yield, and especially benefits the elderly population.

24 Claims, 2 Drawing Sheets

U.S. PATENT DOCUMENTS

| | | |
|---|---|---|
| 5,607,388 | 3/1997 | Ewall . |
| 5,628,724 | 5/1997 | DeBusk et al. . |
| 5,643,188 | 7/1997 | Oliveira ................................. 602/54 |
| 5,709,651 | 1/1998 | Ward . |
| 5,713,842 | 2/1998 | Kay . |
| 5,733,251 | 3/1998 | Johns . |
| 5,755,681 | 5/1998 | Plews ................................. 602/58 |
| 5,780,048 | 7/1998 | Lee . |
| 5,827,530 | 10/1998 | Reed, Jr. . |
| 5,931,800 | 8/1999 | Rasmussen et al. . |

PATCH APPLICATOR

This application is a continuation-in-part of Ser. No. 09/182,654, filed Oct. 30, 1998, which is hereby incorporated by reference herein.

BACKGROUND OF THE INVENTION

This invention relates to a patch applicator system for a transdermal patch which facilitates the application of transdermal patches, particularly transdermal patches having small dimensional characteristics.

A transdermal patch requires intimate contact with the site of application in order to effectively deliver a drug either locally or systemically. Such contact is usually achieved and maintained by means of an adhesive layer on the face of the patch. To protect the adhesive layer prior to application by the patch user, a releasable material is typically laminated to or applied over the adhesive which is then later removed and discarded before use. Removal of the release liner is often difficult without a mechanism to facilitate "peeling" it away from the adhesive.

A prior method used to accomplish this provides the release liner with a score or slit, such that upon bending of the release liner, a corner of the liner is exposed at the location of the slit to allow the liner to be peeled off.

Whether the release liner is scored or cut completely through, precision equipment is required. In addition to having to continually monitor and maintain such equipment, production problems including cracking of the release liner and imperfect or improper depth of the scores or cuts (for example, cutting into the adhesive or entirely through the patch) can occur. Further, even when the release liner is scored or cut as desired, separation from the adhesive layer can still prove to be cumbersome and difficult, particularly as the size of the patch is reduced.

Improvements in transdermal drug delivery technology such as those described in U.S. Pat. Nos. 5,474,783 and 5,656,286 both assigned to Noven Pharmaceuticals, Inc., Miami, Fla., have resulted in the ability to produce smaller and smaller patches without compromising the ability to deliver a therapeutically effective amount of the drug. Smaller patches, those less than 20 $cm^2$ in surface area, and especially those less than 10 $cm^2$, provide many advantages over larger patches.

The larger the patch, the greater the tendency of the patch to wrinkle, fold, become loose and/or dislodge from the application site, all of which reduces its ability to effectively deliver a therapeutic amount of drug or other material. Larger patches, due to their size, offer limited areas on a body for application and are often uncomfortable to wear as well as being unsightly. Since larger patches are more likely to be seen on an individual, the patch user can become more self-conscious or even embarrassed. Larger patches are also more costly to produce due to the need for greater amounts of drug, adhesives, excipients and additives. This in turn increases the risks of irritation and sensitization, especially since the possible application sites are reduced. Larger patches are more cumbersome to apply, adhering to itself or another inappropriate surface such as the fingers of the patch user, once the release liner is removed.

While smaller size patches offer numerous advantages over larger patches, the use of conventional scoring and cutting methods for the release liner creates greater disadvantages. As the size of the patch is reduced, the area that may be grasped when peeling the release liner away is also reduced. Smaller size patches also tend to increase the area of the patch which is touched before application, due to the need to manipulate the patch while the release liner is removed. This can result in loss of adherence before application of the patch. Touching the adhesive also increases risk of contamination to both the application site as well as the patch itself, which can negatively impact proper delivery of the drug or other agent. Further, contamination of the user's hands can result in contamination of sensitive areas of the user, such as the eyes or mouth, if touched by the user after application. Certain segments of the population, such as the elderly or those with arthritic conditions, may further find handling of smaller patches difficult. In view of the foregoing, it will be appreciated that providing a more effective and easily removable release liner would be desirable, particularly for smaller size patches.

SUMMARY OF THE INVENTION

It is therefore an object of this invention to provide a transdermal patch with a release liner which is more easily removed without wrinkling or folding of the transdermal patch.

It is a further object of this invention to provide a grasping mechanism to easily remove the release liner and apply the patch with only one hand.

It is another object of this invention to provide a transdermal system which reduces the problem of touching the adhesive layer when removing the release liner.

The present invention overcomes the problems of the prior art by providing a transdermal patch applicator where the release liner associated with the transdermal patch is especially easy to remove. In general, the patch has a release liner which includes a handling tab(s) or pulltab(s) which aid in removing the release liner from the transdermal patch, as well as in applying the patch to a desired area of the skin or mucosa. A portion of the tab or tabs desirably extend beyond the margin of the transdermal patch to facilitate the handling of the patch. The handling or pulltabs may be formed as separate members secured to the lower release liner at particular locations and configured to allow the release liner to be effectively removed. In an alternative embodiment, the handling tab or tabs may be integrally formed in the release liner itself.

In a preferred embodiment of the invention, a single release liner is releasably affixed to the patch adhesive. The release liner has first and second portions separated by a score or slit, and pulltabs associated with each of the release liner portions. The pulltabs each comprise a first engaging portion and a second actuating region separated by a fold, such that the actuating portion of the pulltabs are folded back upon the engaging portion to be disposed at an acute angle relative thereto. The release liner, as well as pull tabs, are substantially more rigid than the backing layer of the transdermal patch, such that when the patch applicator is operated, the actuating portion of the pulltab will apply an upward force to the release liner to cause release liner will separation of the portions of the liner at the slit. The first pulltab and liner portion may then be removed by continued pulling of the first pulltab. The exposed adhesive layer disposed on the backing layer is applied to the skin or mucosa without the need to manipulate the patch. The second tab is removed by pulling the second pulltab thereafter. The remaining adhesive is then applied to the skin by pressing the backing layer. The construction allows easy handling and application of the transdermal patch by means of the pulltab configuration and interaction with the release liner, particularly with desired smaller patch sizes required by users.

Further features will become more fully apparent in the following description of the embodiments of this invention and from the appended claims.

DETAILED DESCRIPTION OF THE PREFERRED EMBODIMENTS

Figure 1:
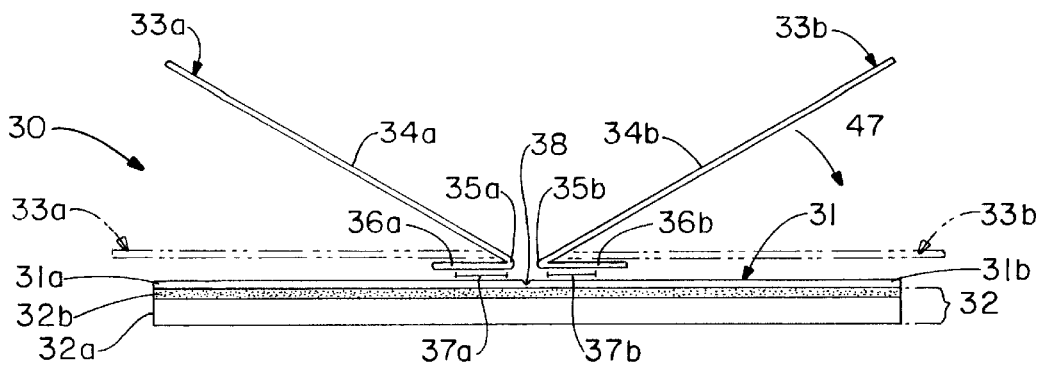
FIG. 1 is a side view of a first embodiment of the invention.
Figure 2:
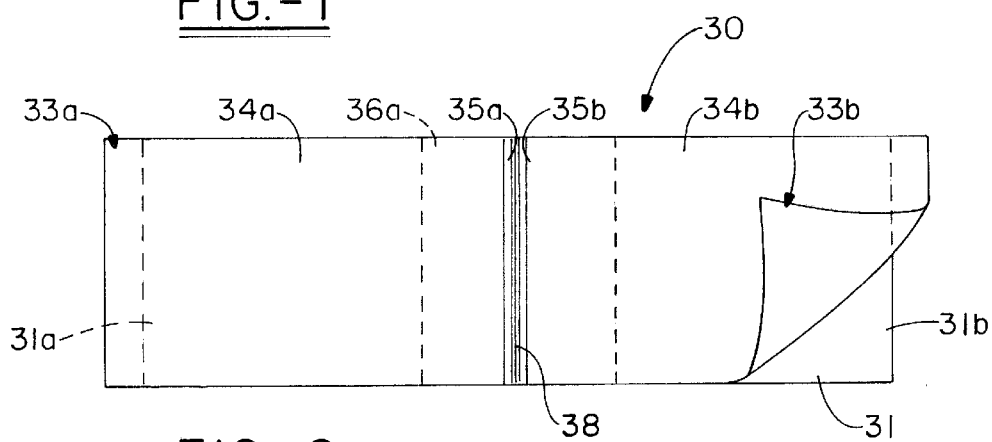
FIG. 2 is a top view of the embodiment shown in FIG. 1.

FIGS. 1 and 2 show a first preferred embodiment of the invention, the transdermal patch applicator being generally indicated at 30. The term transdermal as used herein means passage of a drug through skin or mucosa for localized or systemic delivery. The transdermal patch 32 comprises a backing layer 32a and a patch adhesive layer 32b. A release liner 31 is provided to selectively cover the adhesive layer 32b for shipment and handling, and has a first portion 31a and second portion 31b, which are separated by a weakened zone, to be referred to as a slit 38.

Slit 38 can be a scored line, a separation cut partially or completely through release liner 31, a perforation, or other suitable weakened zone. The slit 38 extends across release liner 31 such that release liner 31 is selectively separable into portions 31a and 31b upon operation of the applicator system. In FIG. 1, slit 38 is shown in an exaggerated view as a score line. Slit 38 is generally centered with respect to release liner 31 such that tabs 31a and 31b are of substantially the same surface area. The particular orientation of slit 38 with respect to the transverse and lateral axes of release liner 31 is not critical, and tabs 31a and 31b can be of unequal surface area. Slit 38 can therefore be parallel to the transverse or lateral edges of release liner 31 or can be placed at an angle from the parallel. Alternatively, slit 38 can be centered with respect to the transverse or lateral dimension of release liner 31, or slit 38 can be offset from center.

The backing layer 32a is preferably substantially impermeable and occlusive to water vapor transmission, serves to retain and maintain the patch adhesive layer 32b disposed thereon in a defined size and shape. The backing layer 32a also prevents loss of the drug and/or enhancers to the environment, renders the patch (in conjunction with the release liner) transportable, and generally provides protection both prior to and after application of the patch to the user.

Suitable materials that can be used singularly or in combination, as laminates or as coextrusions, to form the backing layer are well known in the art and include films or sheets of polyethylene, polyester, polypropylene, polyurethane, polyolefin, polyvinyl alcohol, polyvinyl chloride, polyvinylidene, polyamide, polycarbonate, polystyrene, vinyl acetate resins, BAREX®, ethylene/vinyl acetate copolymers, ethylene/ethylacrylate copolymers, metal-vapor deposited films or sheets thereof, rubber sheets or films, expanded synthetic resin sheets or films, non-woven fabrics, fabrics, knitted fabrics, clothes, foils and papers.

The backing layer generally has a thickness in the range of 2 to 5 mils or the like, and is flexible. The backing layer may be pigmented, for example colored to either match with or conversely easily distinguish from the site of application, and/or contain printing, labeling and other means of identification and/or tracability of the patch itself. The backing layer may further be made opaque or substantially opaque (i.e., preventing light or certain energy wavelengths from penetrating or passing through), such as by metallization, fillers, inks, dyes and the like, for purposes of protecting photosensitive active agents from degradation and/or preventing photoallergic reactions or irritations on the subject.

Release liner 31 is preferably made from suitable materials to protect the adjacent patch adhesive layer 32b. The release liner 31 is also intended to prevent loss of the drug and/or enhancers to the environment, and render the individual patch (in conjunction with the backing layer) transportable as well as generally protect the patch from contamination and the like until its application by the user. The release liner 31 is typically also substantially impermeable and occlusive, and must be compatible with the particular adhesives and/or drugs so as not to interfere with their ultimate application and therapeutic effect.

Suitable materials that can be used singularly or in combination, as laminates or as coextrusions, to form the release liner are also well known in the art, for example cellophane, nylon, glassine paper, acrilonitrile or acrylic copolymers, and include any material suitable for use as the backing layer. When the release liner is composed of a material which typically does not readily release (i.e., is not easily removed or separated from the patch adhesive layer), for example paper, a coating material such as a silicone, teflon or thermoplastic materials such as polyester, polyvinyl resin, polyethylene or cellulose acetate, may be applied to the release liner by any conventional means. Preferred release liners are polyester films, particularly commercially available silicone coated films. Suitable films are manufactured by DuPont, Wilmington, Del., under the trademark Mylar® and fluropolymer and silicone coated films commercially available from Rexam Release, Oak Brook, Ill. under the trademark FL2000® and MRL2000®, and from 3M Corporation, St Paul, Minn. under the trademark Scotch-Pak® 1012 or ScotchPak® 1022.

Preferably, release liner 31 is constructed such that release liner 31 is substantially more rigid than backing layer 32a. Being substantially more rigid, upon operation of the pulltab system as will be described, the force applied to release liner 31 will be focused on the region of slit 38 to cause separation of portions 31a and 31b. As the backing layer 32a will bend easily while release liner 31 remains rigid the patch user can easily remove a portion 31a or 31b to expose a portion of the patch adhesive layer 32b by operation of the associated pulltab, while holding only the other pull tab. No manipulation of the backing layer 32a is required, which is particularly important with respect to application of the desired smaller patch sizes.

Pulltabs 33a and 33b are affixed to each portion of the release liner 31 at regions 36a and 36b, respectively. In order to achieve removal of release liner 31 with a transdermal patch, particularly transdermal patches, it was necessary to have each pulltab comprise two distinct regions. As shown in FIG. 1, pulltab 33a comprises regions 34a and 36a separated by a bend 35a, and pulltab 33b comprises portions 34b and 36b separated by bend 35b. In this configuration, the regions 34a and 34b extend outwardly from transdermal patch 32 at an acute-angle relative to regions 36a and 36b. This configuration, which may be referred to as a "butterfly" configuration, accomplishes two critical purposes. First, it allows the user to easily grasp pulltab portions 34a and 34b in order to remove each portion of the release liner 31, which further reduces excessive handling of the transdermal patch.

Without regions 36a and 36b, each pulltab would otherwise be flat or planar relative to release liner 31. Separation of the pulltab from the release liner would be burdensome and clumsy. Second, removal of each portion of the pulltabs 33a and 33b requires an angular force which is achieved by means of bends 35a and 35b. Attempting to remove each portion of release liner 31 using a lateral force (i.e., if pulltabs 33a and 33b lacked regions 36a and 36b and bends 35a and 35b) is virtually impossible, especially if slit 38 is scored rather than completely separated, without risking damage to the transdermal patch 32.

For ease of production and packaging of a finished transdermal product, pulltabs 34a and 34b can be scored along a region from bends 35a and 35b to a point about midway along regions 34a and 34b, to permit regions 34a and 34b to lie substantially planar or parallel to release liner 31 until use is desired, such as shown by arrow 47 and the broken lines in FIG. 1

Pulltabs 33a and 33b may be fabricated from the same materials suitable for use as release liner 31, and are typically in a range of from about 3 to 6 mils in thickness, depending on the materials used, in order to facilitate handling and resist tearing during use.

Pulltabs 33a and 33b are affixed to portions 31a and 31b, respectively. In the embodiment as shown in FIG. 1, region 36a of pulltab 33a is affixed to tab 31a at adhesion point 37a, and region 36b of pulltab 33b is affixed to tab 31b at adhesion point 37b. The pulltabs are affixed using a suitable adhesive similar to the adhesive used in layer 32b. Alternatively, pulltabs 33a and 33b may be affixed to portions 31a and 31b, respectively, using thermobonding or fusion bonding, or other attachment means as is known in the art. In use, pulltabs 33a and 33b remain affixed to portions 31a and 31b, so the adhesive thermobonding, fusion bonding, or other attachment means must be adequate to keep the pulltabs affixed to the release liner portions when in use.

Figure 3:
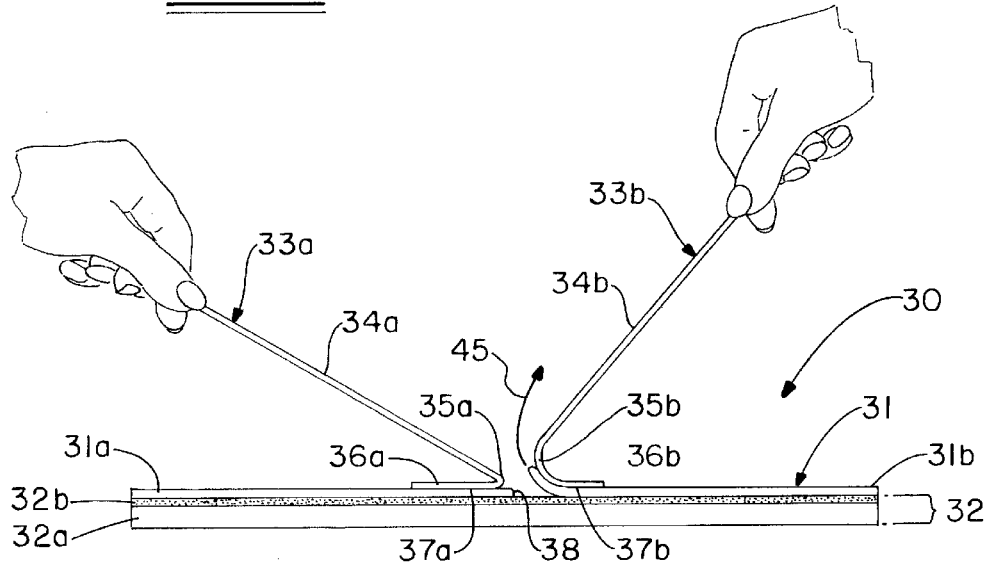
FIG. 3 is a side view of the patch applicator system being operated.

During use as shown in FIG. 3, a patch user initially grasps the patch applicator 30 by means of pulltabs 33a and 33b to separate the portions 31a and 31b at slit 38. Again, this function is provided by forming release liner 31 and pulltabs 33a and 33b to have substantially more rigidity than the backing layer 32a. One of the pulltabs is grasped in the region 34a or 34b and pulled, such that the force applied by the user is translated to the area adjacent bend 35a or 35b. This force is directed outwardly at this location as shown by arrow 45, due to affixation of portion 36 to liner 31 and the acute angle at which region 34 extends outwardly therefrom. The preferred angle at which force will be applied is between 30 to 60 degrees. As the user holds regions 34a and 34b, pulling on one will exert force directly on the release liner 31 adjacent slit 38, which due to its relatively rigid construction, will rupture or separate the liner 31 along the slit 38 to remove the affixed portion 31a or 31b. This exposes a portion of the patch adhesive layer 32b covered by the removed tab. While holding onto the remaining pulltab, the exposed adhesive is applied to the skin or mucosa and pressed down using a single hand. The remaining pulltab 33a or 33b is then removed by pulling on the pulltab section 34 to expose the remaining adhesive, and the remaining exposed adhesive of the transdermal patch is then pressed down against the skin or mucosa.

To aid in grasping the pulltabs 33a and 33b, regions 34a and 34b preferably extend beyond an edge of the transdermal patch 32. Particularly for small patches of are less than about 20 cm$^2$, nonextended pulltabs may be so short as to inhibit easy manipulation, especially by older people. One or both of the pulltabs 33a and 33b therefore preferably extend beyond an edge or end margin of the transdermal patch. Having pulltabs 33 of this configuration further facilitates removal of the release liner along slit 38 by providing leverage to the pull force of the user. Upon initial actuation, the force applied to the release liner is again directed outwardly, causing rupture or separation of slit 38 and overcoming the peel strength of the adhesive layer 32b. The pulltab 33 facilitates removal of release liner 31 by allowing the user to apply force to the release liner in the most effective direction for removal at all locations along the length of portion 31a or 31b.

Figure 4:
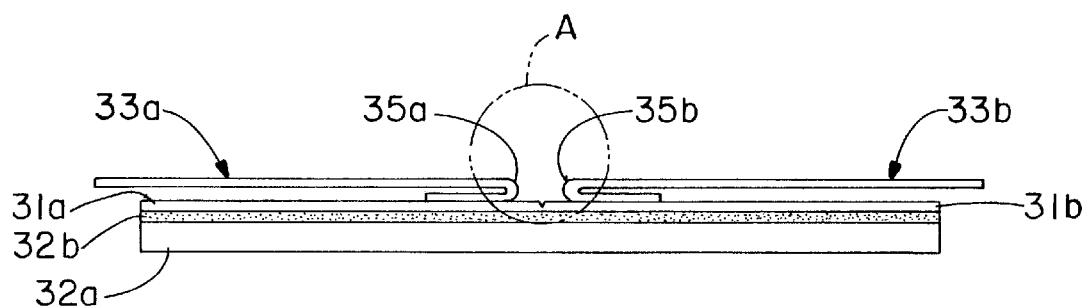
FIG. 4 is a side view of a second embodiment of the invention.
Figure 4A:
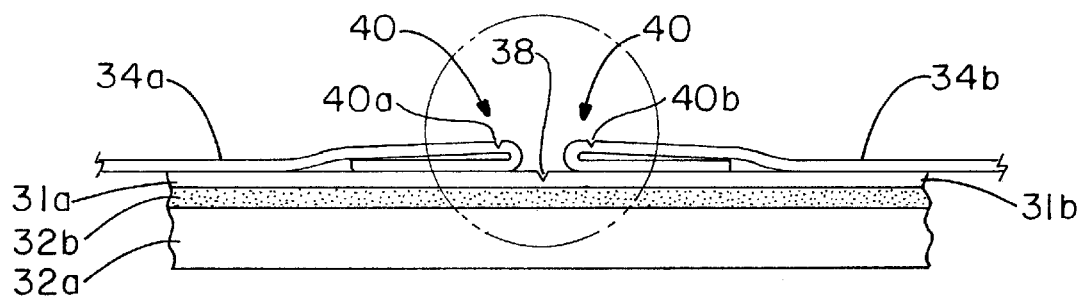
FIG. 4A is a detail view of the encircled portion of FIG. 3.

In another embodiment as shown in FIG. 4 and 4A, the patch applicator system is modified so that the extending pulltab portions 34a or 34b are made to lay flatter against the release liner 31 for handling during manufacture and subsequent packaging of the finished transdermal product after assembly of all the patch components. As transdermal patches according to the invention are designed to be manufactured by automated equipment and assembly processes as well as automated packaging methods, the patch applicator design must preferably accommodate such automated processes. In this embodiment, in addition to or conjunction with the bends 35a and 35b, a score region 40 about the edge of the section 34 including and adjacent to the bend 35 can include a score line generally indicated at 40a and 40b. The extent of the region 40 may not be critical, as the benefits of this embodiment may be realized from positioning of the score lines 40a and 40b at a variety of locations, preferably in the region from the folds to approximately one half of the length of the section 34. The score lines 40a and 40b are produced to allow the sections 34 of the pulltab to function as follows. The use of the score lines 40a and 40b provides a flattened zone in the material of the pulltabs 33, which in turn allows the regions 34a and 34b to fold over to a greater degree. The sections 34a and 34b will then lie more closely adjacent the release liner 31 as shown in the Figures, when no force is applied to the top thereof. During manufacture, this positioning of pulltabs 33 allows simplified contacting and manipulation of the patch or the components during automated assembly, and also facilitates packaging by automatic packaging equipment. The score lines 40a and 40b will tend to maintain the bends 35a and 35b in the folded position to avoid the possibility of unfolding during assembly, leading to problems in manufacturing and packaging. Score lines 40a and 40b are therefore made sufficiently deep into the material to promote folding of the pulltabs but shallow enough to prevent easy tearing of the pulltabs along the score lines. The score lines 40a and 40b can be formed anywhere in the region 40 to operate in this manner. During operation of the patch applicator system, the pulltab section 34a and 34b are then easily disposed at the desired angle of orientation with respect to the release liner 31 as previously described for separating the portions 33a and 33b at slit 38. These portions can then be removed for application of the exposed adhesive to the skin or mucosa. It should be recognized that upon pulling of the pulltab section 34a or 34b, the force will be translated through the score lines 40a and 40b at a direction substantially perpendicular to the score line, such that the force will be distributed along the score line. Therefore, there will be no tendency for the pulltab 33 to tear or rip along score line 40a or 40b, and the force will effectively be transferred to the release liner 31 as desired.

Alternatively, the pulltabs 33 can comprise a single region with no fold or more preferably may comprise a fold such that at least a portion of the pulltab extends away from the adjacent release liner surface. In the former case, the single region of the pulltab is affixed to the tab in a manner substantially the same as shown for the region 36a or 36b in FIG. 1, but without the bends 35a,b, or regions 34a,b. The single region pulltab can extend beyond an end margin of the patch. In the latter alternative, the bends would create an outwardly extending portion, but the pulltab would not be folded upon itself as shown in the preferred embodiment. Such embodiments may minimize the potential problem of unfolding of the bends 35a and 35b in a manner that would adversely effect an automated manufacturing. In the preferred embodiments, the inclusion of the bends 35a and 35b, and the two regions 34ab, and 36ab, ensures the force needed to remove the tab while pulling the pulltabs is more efficiently applied, but suitable configurations of these alternate embodiments may be suitable for a given application. In addition, with the folded pulltab configuration, the pulltab is less likely to experience failure of the adhesive or other attachment means, and resulting detachment of the pulltab from the tab, during manipulation of the pulltab.

The transdermal patch applicator and transdermal patches of this invention can be of any suitable shape, including square, rectangular, circular, oval, or irregularly shaped.

Suitable adhesives for use as the patch adhesive layer are intended in their broadest sense to mean any natural or synthetic polymer that is capable of sticking to the site of application, and include bioadhesives (also referred to a mucoadhesives) and pressure-sensitive adhesives as are generally known in the art. The term pressure-sensitive refers to a viscoelastic material which adheres instantaneously to most surfaces with the application of very slight pressure and remains permanently tacky. A polymer is an adhesive within the meaning of the term if it has the properties of an adhesive per se or if it functions as an adhesive by the addition of tackifiers, plasticizers, cross-linking agents or other additives. Especially preferred adhesives are polyurethanes, polyisobutylenes, acrylics, vinyl acetates, natural and synthetic rubbers, natural and synthetic gums, polysiloxanes, polyacrylates, ethylene/vinyl acetate copolymers, polyvinylpyrrolidones, vinylpyrrolidone copolymers and particularly vinyl pyrrolidone/vinylacetates, styrene block copolymers, and mixtures thereof. Presently preferred adhesives are polyacrylates, polysiloxanes, polyisobutylenes and mixtures thereof. Particularly suitable bioadhesives or mucoadhesives include natural or synthetic polysaccharides and polyacrylic acid polymers, and mixtures thereof. The term "polysaccharide" as used herein means a carbohydrate decomposable by hydrolysis into two or more molecules of monosaccharide or their derivatives. Preferred polysaccharides include cellulose materials and natural gums. Such adhesives may be used singularly, or in blends of two or more. Typically, the patch adhesive layer 32b serves as the carrier for the drug, drugs or other active agent to be administered to the patch user. Alternatively, additional layers (not shown) may be included between the patch adhesive layer 32b and the backing layer 32a, which layers may or may not also be adhesives or incorporate one or more drugs, and include any of the non-toxic polymers well known in the art used to carry drugs or act as rate-controlling membranes. Patch adhesive layer 32b is preferably a continuous layer, but may be discontinuous as long as the drug may be administered as is necessary to effect therapy.

The layers of transdermal patch 32, other than the backing layer 32a, can also contain agents known to accelerate the delivery of a drug through the skin or mucosa. These agents have been referred to as skin-penetration enhancers, accelerants, adjuvants, and sorption promoters, and are herein referred to collectively as "enhancers." This class of agents includes those with diverse mechanisms of action including those which have the function of improving the solubility and diffusibility of a drug within the multiple polymer and those which improve percutaneous adsorption, for example, by changing the ability of the stratum corneum to retain moisture, softening the skin, improving the skin's or mucosa's permeability, acting as penetration assistants or han-follicle openers or changing the state of the skin or mucosa including the boundary layer. Some of these agents have more than one mechanism of action, but in essence they serve to enhance the delivery of a drug.

In addition to enhancers, there may also be incorporated various pharmaceutically acceptable additives and excipients available to those skilled in the art. These additives include tackifying agents such as aliphatic hydrocarbons, mixed aliphatic and aromatic hydrocarbons, aromatic hydrocarbons, substituted aromatic hydrocarbons, hydrogenated esters, polyterpenes and hydrogenated wood rosins, binders such as lecithin which "bind" the other ingredients, rheological agents (thickeners) containing silicone such as famed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, for purposes of enhancing the uniform consistency or continuous phase of the final composition; and other additives and excipients such as diluents, stabilizers, fillers, clays, buffering agents, biocides, huinectants, antiirritants, antioxidants, preservatives, flavoring agents, colorants, pigments and the like.

Illustrative examples of suitable adhesives, enhancers and other additives and excipients are described in U.S. Pat. Nos. 5,474,783, and 5,656,386 both assigned to Noven Pharmaceuticals, Inc, Miami, Fla., and are incorporated herein by reference.

As used herein, the term "drug" is intended to have its broadest interpretation as any therapeutically, prophylactically, pharmacologically or physiologically beneficial active substance, or mixture thereof, which is delivered to a living organism to produce a desired, usually beneficial, effect. More specifically, any substance which is capable of producing a pharmacological response, localized or systemic, irrespective of whether therapeutic, diagnostic, or prophylactic in nature, in animals is within the contemplation of the term. Also within the contemplation of the term are such agents as insect repellents, sun screens, cosmetic agents, etc. It should be noted that the drugs may be used singly or as a mixture of two or more such agents, and in amounts sufficient to prevent, cure, diagnose or treat a disease or other condition, as the case may be. A therapeutically effective amount as used herein is intended to mean the amount of drug sufficient to produce the desired effect, local or systemic, over the duration of intended use of the transdermal patch.

Although the invention has been described and illustrated with respect to certain preferred embodiments, it should be understood that the description is for illustration and example only, and is not meant to limit the spirit and scope of this invention

What is claimed is:

1. A transdermal patch comprising:
    a patch adhesive layer including a therapeutically effective amount of at least one drug to be delivered to a patient and a backing layer;

a release liner releasably affixed to said patch adhesive layer, said release liner substantially covering said adhesive layer until removal for application, and comprising a first portion, a second portion, and a slit separating said first and second portions; and first and second pulltabs, wherein said first pulltab is affixed to said first portion of said release liner, and said second pulltab is affixed to said second portion of said release liner.

2. The transdermal patch of claim 1, wherein said slit is a score line.

3. The transdermal patch of claim 1, wherein said slit is completely cut through said release liner.

4. The transdermal patch of claim 1, wherein at least one of said pulltabs extends beyond an end margin of said transdermal patch.

5. The transdermal patch of claim 1, wherein said first and second pulltabs each comprise a first region and a second region, wherein said first and second regions are separated by a fold.

6. The transdermal patch of claim 5, said fold comprises a score line.

7. The transdermal patch of claim 5, wherein said first region of said first pulltab is affixed to said first portion, and said first region of said second pulltab is affixed to said second portion.

8. The transdermal patch of claim 5, wherein said second regions of said first and second pulltabs are folded upon said first regions so as to extend outwardly from said release liner at an acute angle from said first portions.

9. The transdermal patch of claim 1, wherein said transdermal patch has an area of 20 $cm^2$ or less.

10. The transdermal patch of claim 1, wherein said transdermal patch has an area of 10 $cm^2$ or less.

11. The transdermal patch of claim 1, wherein said patch adhesive layer comprises a drug.

12. The transdermal patch of claim 1, wherein said release liner is substantially more rigid than said backing layer.

13. The transdermal patch of claim 1, wherein said release liner is fabricated from at least one material selected from the group consisting of cellophane, nylon, glassine paper, acrylonitrile polymers, acrylic polymers, paper, silicones, fluoropolymers, polyesters, polyvinyl resins, polyethylene, and cellulose acetate.

14. The transdermal patch of claim 1, wherein said release liner has a thickness of from about 3 mils to about 6 mils.

15. The transdermal patch of claim 1, wherein said pulltabs are affixed with an adhesive.

16. The transdermal patch of claim 1, wherein said pulltabs are affixed by thermobonding or fusion bonding.

17. The transdermal patch of claim 1, wherein said first tab and said second tab are of unequal areas.

18. The transdermal patch of claim 5, wherein said fold creates an angle of approximately 30 to 60 degrees between said first and second portions of said pulltabs.

19. A transdermal patch comprising:

a patch adhesive layer and a backing layer on which said patch adhesive layer is provided;

a release liner releasably affixed to said patch adhesive layer, said release liner comprising first and second portions and a slit separating said first and second portions, said release liner being substantially more rigid than said backing layer; and first and second pulltabs, said pulltabs each comprising first and second ends with a first end adapted to be grasped by a user, and a second end affixed to one of said first and second portions of said release liner adjacent said slit, wherein said pulltabs are pulled by the user to translate a pulling force to said second end of said pulltab to cause separation of said first and second portion of said release liner at said slit due to the different rigidity of said release liner relative to said backing layer.

20. The transdermal patch of claim 19, wherein said transdermal patch has an area of 20 $cm^2$ or less.

21. The transdermal patch of claim 19, wherein said release liner has a thickness of from about 3 mils to about 6 mils.

22. The transdermal patch of claim 19, wherein said release liner has first and second sections having a bend therebetween, said second section being folded about said bend so as to be disposed at an acute angle relative to said first section for use.

23. The transdermal patch of claim 19, wherein said fold comprises a score line.

24. The transdermal patch of claim 19, wherein at least one of said pulltabs extends beyond an end margin of said transdermal patch.

* * * * *